United States Patent [19]
Johnson et al.

[11] Patent Number: 5,359,087
[45] Date of Patent: Oct. 25, 1994

[54] BIOACTIVE QUISQUALIC ACID ANALOGS

[75] Inventors: Rodney L. Johnson; Nalin L. Subasinghe, both of Minneapolis; James F. Koerner, Columbia Heights, all of Minn.

[73] Assignee: Regents of the University of Minnesota, Minneapolis, Minn.

[21] Appl. No.: 72,033

[22] Filed: Jun. 3, 1993

[51] Int. Cl.$^5$ ............... C07D 207/404; C07D 207/448
[52] U.S. Cl. .................................. 548/546; 548/548; 548/549
[58] Field of Search ........................ 548/546, 548, 549

[56] References Cited

PUBLICATIONS

J. D. Davies et al., "Excitatory Amino Acid Receptors and Synaptic Excitation in the Mammalian Central Nervous System", *J. Physiol.*, 75, 641–654 (1979).
T. Honore et al., "The Binding of [$^3$H]AMPA, a Structural Analogue of Glutamic Acid, to Rat Brain Membranes", *J. Neurochem.*, 38, 173 (1982).
R. L. Johnson et al., "Excitatory Amino Acid Neurotransmission", *J. Med. Chem.*, 31, 2057 (1988).
E. D. London, "Specific Binding of [$^3$H]Kainic Acid to Receptor Sites in Rat Brain", *Mol. Pharmacol.*, 15, 492 (1979).
D. J. Monaghan et al., "The Excitatory Amino Acid Receptors: Their Classes, Pharmacology, and Distinct Properties in the Function of The Central Nervous System", *Annu. Rev. Pharmacol. Toxicol.*, 29, 365 (1989).
M. Recasens et al., "A New Quisqualate Receptor Subtype (sAA$_2$) Responsible for the Glutamate-Induced Inositol Phosphate Formation in Rat Brain Synaptoneurosomes", *Neurochem. Int.*, 13, 463 (1988).
M. B. Robinson et al., "Exposure of Hippocampal Slices to Quisqualate Sensitizes Synaptic Responses to Phosphonate-Containing Analogues of Glutamate", *Brain Res.*, 381, 187 (1986).
M. B. Robinson et al., "Hydrolysis of the Brain Dipeptide N-Acetyl-L-aspartyl-L-glutamate", *J. Biol. Chem.*, 262, 14498 (1987).
D. D. Schoepp et al., "Excitatory Amino Acid Agonist-Antagonist Interactions at 2-Amino-4-Phosphonobutyric Acid-Sensitive Quisqualate Receptors Coupled to Phosphoinositide Hydrolysis in Slices of Rat Hippocampus", *J. Neurochem.*, 50, 1605 (1988).
M. K. Schulte et al., "Structure-function Relationships for Analogues of L-2-Amino-4-phosphonobutanoic Acid on the Quisqualic Acid-Sensitive AP4 Receptor of the Rat Hippocampus", *Brain Res.*, 582, 291 (1992).

4,677,318   6/1987  Veenstra ........................ 307/465

(List continued on next page.)

*Primary Examiner*—David B. Springer
*Attorney, Agent, or Firm*—Schwegman, Lundberg & Woessner

[57] ABSTRACT

The present invention provides bioactive compounds of the general formula:

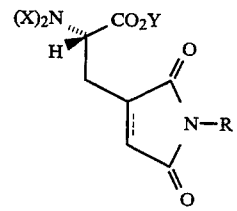

wherein R is H, $(C_1-C_4)$alkyl, $(C_3-C_6)$cycloalkyl, $(C_3-C_6)$cycloalkyl$(C_1-C_4)$alkyl, allyl, $(C_6-C_{10})$aryl or $(C_1-C_4)$alkylCO$_2$Y; Y is H, $(C_1-C_4)$alkyl or $(C_6-C_{10})$aryl; each X is individually H, $(C_1-C_4)$alkyl, $(C_6-C_{10})$aryl, $(C_3-C_6)$cycloalkyl$(C_1-C_4)$alkyl, or $(C_3-C_6)$cycloatkyl; the bond represented by—is present or is absent; and the pharmaceutically acceptable salts thereof, and methods for using said compounds to stimulate receptors in the mammalian nervous systems.

15 Claims, 2 Drawing Sheets

PUBLICATIONS

M. J. Sheardown et al., "A New and Specific Non-NMDA Receptor Antagonist, FG 9065, Blocks L-AP4-evoked Depolarization in Rat Cerebral Cortex", *Eur. J. Pharmacol.*, 148, 471 (1988).

E. R. Whittemore, "Novel Recognition Site for L--Quisqualate Sensitizes Neurons to Depolarization by L-2-amino-4-phosphonobutanoate (L-AP4)", *Brain Res.*, 485, 146–156 (1989).

E. R. Whittemore et al., "Pre-exposure to L-homocysteinesulfinic Acid Blocks Quisqualate-induced Sensitization to L-2-amino-4-phosphonobutanoic Acid", *Eur. J. Pharmacol.*, 192, 435 (1991).

R. Zaczek et al., "Characteristics of Chloride-Dependent Incorporation of Glutamate into Brain Membranes Argue Against a Receptor Binding Site", *Neuropharmacol.* 26, 281 (1987).

R. J. Roon et al., "Synthesis of Quisqualic Acid Analogues as Possible Selective Ligands at Quisqualic Acid Receptors", *Soc. Neuroscience Abstracts*, 18, 649, Abstract No. 277.16 (1992).

N. Subasinghe et al., "Synthesis of Quisaqualic Acid Analogues as Possible Selective Ligands at Quisqualic Acid Receptors", *23rd National Medicinal Chemistry Symposium*, Buffalo N.Y., Abstract No. 12 (1992).

N. Subasinghe et al., "Quisqualic Acid Analogues: Synthesis of beta-Heterocyclic 2-Aminopropanoic Acid Derivatives and Their Activity at a Novel Quisqualate-Sensitized Site", *J. Med. Chem.*, 35, 4602–2607 (1992).

BIOACTIVE QUISQUALIC ACID ANALOGS

The present invention was made with the support of the U.S. Government under NIH Grant No. NS 17944. The U.S. Government has certain rights in the invention.

BACKGROUND OF THE INVENTION

Neuronal conduction across synapses in the mammalian central nervous system (CNS) is facilitated by a wide array of neurotransmitters. These neurotransmitters, upon release from the presynaptic neuron, can be either inhibitory or excitatory in action, depending upon whether they hyperpolarize or depolarize the postsynaptic neuron, respectively. Glutamic acid and aspartic acid have been identified as the major millisecond excitatory neurotransmitters in the mammalian CNS by R. L. Johnson et al., *J. Med. Chem.*, 31, 2057 (1988). Five excitatory amino acid (EAA) receptor subtypes have been characterized so far. receptor subtypes have been characterized so far. See D. J. Monaghan et al., *Annu. Rev. Pharmacol. Toxicol.*, 29, 365 (1989). These are the NMDA, AMPA, kainate, metabotropic, and L-AP4 receptors. The first three EAA receptor types directly gate ion channels, while the last two receptor types operate via second-messenger systems.

L-Quisqualic acid (1), an amino acid first isolated from the seeds of *Quisqualis indica* L., is a unique compound in that it is able to function as an agonist at multiple EAA receptor subtypes in the CNS.

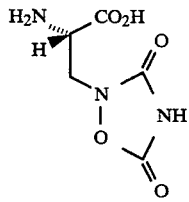

It has high affinity for the kainate, AMPA, and the metabotropic receptors. For example, see J. D. Davies et al., *J. Physiol.*, 75, 641 (1979); E. D. London, *Mol. Pharmacol.*, 15, 492 (1979); T. Honore et al., *J. Neurochem.*, 38, 173 (1982); D. D. Schoepp et al., *J. Neurochem.*, 50, 1605 (1988) and M. Recasens et al., *Neurochem. Int.*, 13, 463 (1988). L-Quisqualic acid also inhibits the $Ca^{2+}/Cl^-$-dependent glutamic acid uptake system in brain synaptic plasma membrane preparations and an N-acetyl α-linked acidic dipeptidase which hydrolyzes the brain dipeptide Ac-Asp-Glu-OH. See, R. Zaczek et al., *Neuropharmacol.*, 26, 281 (1987) and M. B. Robinson et al., *J. Biol. Chem.*, 262, 14498 (1987).

Recently, L-quisqualic acid has been shown to produce a 30-100-fold sensitization of CA1 neurons in rat hippocampal slices to depolarization (excitation) by D- or L-2-amino-4-phosphonobutanoic acid (AP4) and related phosphonates. See, M. B. Robinson et al., *Brain Res.*, 381, 187 (1986) and E. R. Whittemore, *Brain Res.*, 486, 146 (1989). This phenomenon, which has been termed the QUIS effect, appears to be widely distributed, and has been reported for neurons of the CA1 region in the rat and guinea pig brain and the medial perforant path, the lateral olfactory tract, and the cingulate cortex in rat brain. See E. R. Whittemore et al., *Brain Res.*, 489, 146 (1989) and M. J. Sheardown et al., *Eur. J. Pharmacol.*, 148, 471 (1988). E. R. Whittemore et al., *Eur. J. Pharmacol.*, 192, 435 (1991) have reported that the QUIS effect can be blocked by a brief exposure of CA1 neurons to L-homocysteinesulfinic acid, L-α-aminoadipic acid, or L-serine O-sulfate. These compounds have been ntermed "preblockers" since they are able to block the QUIS effect even when they are removed from the incubation chamber prior to treatment of the slices with L-quisqualic acid. These same compounds are also capable of reversing the QUIS effect after it has been induced. Thus, these compounds are also referred to as "reversers." The AP4 site which is sensitized by L-quisqualic acid and the site to which L-quisqualic acid binds in order to bring about this sensitization are novel sites of action different from the classical AMPA and L-AP4 sites (M. K. Schulte et al., *Brain Res.*, 582, 291 (1992)).

Since the dramatic increase of neuronal excitability manifested by the QUIS effect may have significance for understanding and modifying the mechanisms of neuronal plasticity that occur during learning and memory and for controlling the changes of excitability that occur in disease states such as epilepsy, a need exists for novel bioactive analogs of L-quisqualic acid.

SUMMARY OF THE INVENTION

The present invention provides bioactive analogs of L-quisqualic acid of the general formula (I):

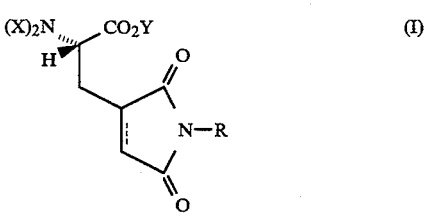

wherein R is H, $(C_1-C_4)$alkyl, $(C_3-C_6)$cycloalkyl, $(C_3-C_6)$-cycloalkyl $(C_1-C_4)$alkyl, allyl, $(C_6-C_{10})$aryl or $(C_1-C_4)$-alkyl$CO_2Y$; Y is H, $(C_1-C_4)$alkyl or $(C_6-C_{10})$aryl; each X is individually H, $(C_1-C_4)$alkyl, $(C_6-C_{10})$aryl, $(C_3-C_6)$cycloalkyl $(C_1-C_4)$alkyl or $(C_3-C_6)$cycloalkyl; the bond represented by—is present or is absent; and the pharmaceutically acceptable salts thereof.

Preferably, R is H, $(C_1-C_4)$alkyl, alkoxycarbonyl($C_1-C_4$)alkyl or carboxy($C_1-C_4$)alkyl, i.e., $CH_2CO_2Y$, most preferably, R, Y and each X is H or $(C_1-C_4)$alkyl, i.e., $N(X)_2$ is $NH_2$. The substituent $(C_6-C_{10})$aryl includes phenyl, $(C_1-C_4)$alkylphenyl, phenyl $(C_1-C_4)$alkyl and [bis($C_1-C_2$)alkyl]phenyl, i.e., tolyl, phenethyl, benzyl and the like. Preferably, $(C_3-C_6)$cycloalkyl($C_1-C_4$)alkyl is cyclopropylmethyl. The term $(C_1-C_4)$alkyl encompasses isopropyl, isobutyl and t-butyl.

In formula I, in FIG. 1 and in Scheme I, a bond represented by a dashed line extends below the plane of the sheet and a bond represented by a wedged line extends above the plane of the sheet. A bond represented by a waved line indicates a mixture of configurations at the given center.

Pharmaceutically acceptable salts include the acid addition salts of inorganic acids or organic acids to the $N(X)_2$, i.e., the hydrochloride, phosphate, sulfate, tartarate, malate, maleate, oxalate, citrate or butyrate salts of the compound of formula I, as well as carboxylic acid salts wherein the moiety Y is an equivalent of an alkali metal cation, an alkaline earth metal cation, $(NH_4)^+$ or $(N(X)_4)^+$, wherein X is as defined above. These salts can be readily prepared by methods known to the art, e.g., by reacting NH2 groups with halides such as XCl in the presence of an organic base or by reacting CO2H groups with alcohols such as YOH in the presence of acid or base, wherein X and Y are as defined above, and are other than H. Basic salts of the ring NH group can also be prepared, i.e., of the formula NY, wherein Y is not H.

When dissolved in a pharmaceutically acceptable liquid vehicle and contacted with mammalian tissue comprising neurons which have been presensitized by exposure to L-quisqualic acid, the bioactive compounds of formula I exhibit an increased ability to depolarize (excite or stimulate) the neurons, over their ability to do so in the absence of quisqualic acid conditioning. The general mechanism believed to be operative in the QUIS effect is shown in FIG. 2. Since neurons which can be sensitized by quisqualic acid are widely distributed, the present compounds can be used to stimulate neurons in the central nervous system (CNS) and the peripheral nervous system, i.e., in the brain, spinal cord and the olfactory tract of mammals, including man, either in vitro or in vivo. Furthermore, certain of the compounds of the invention are also active at the AMPA neuronal receptor subtype. Thus, the present compounds may be used directly to treat or ameliorate neuronal disorders such as epilepsy, Huntington's chorea, Alzheimer's disease, memory/learning disorders, smell/taste disorders, or may be used indirectly, to enhance the sensitivity of these neurons to other bioactive compounds, such as huperzine A, neuronal growth factor, acetyl choline and bioactive analogs thereof.

DETAILED DESCRIPTION OF THE INVENTION

A. Synthesis of Quisqualic Acid Analogs

Five preferred embodiments of the present invention are shown as compounds 2, 3, 4, 5A, and 5B on Table 1, below.

TABLE 1

Quisqualic Acid Analogs

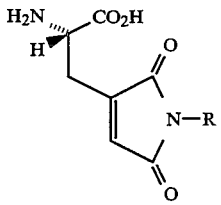

2: R = H
3: R = CH3
4: R = CH2CO2H

TABLE 1-continued

Quisqualic Acid Analogs

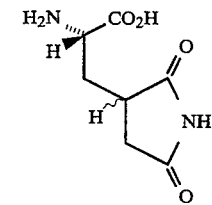

5A: isomer A
5B: isomer B

These compounds are formally 3-(1H-pyrrol-3-yl)- or 3-(pyrrolidin-3-yl)-substituted α-amino-propionic acids, which have the S-configuration at the α-position and, in the case of 5A and 5B, an unassigned configuration (R or S) at the 3-position of the pyrrolidine ring.

Figure 1:
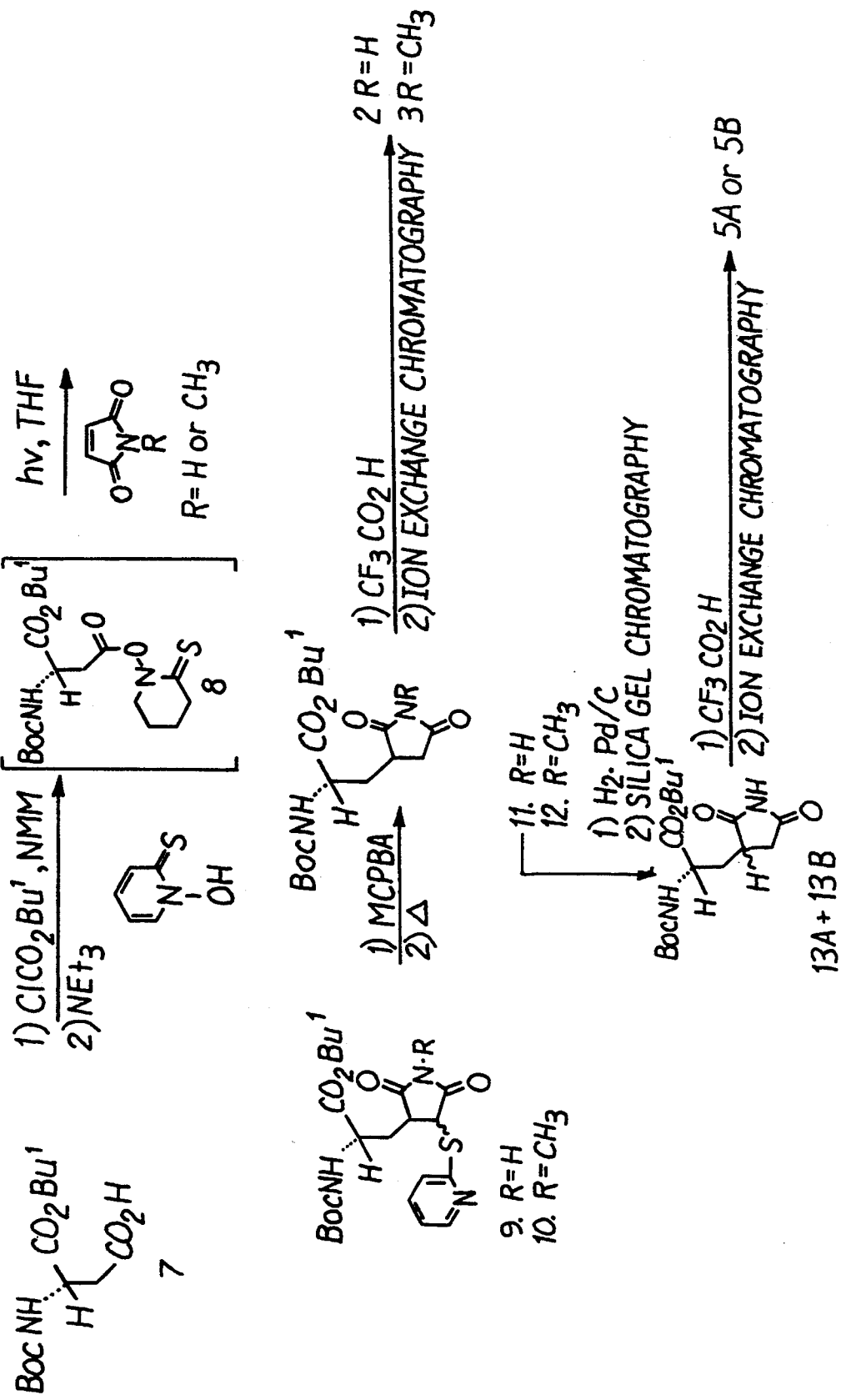
FIG. 1 is a schematic outline of the synthesis of four of the compounds of the present invention (2, 3, 5A, 5B).

As shown in FIG. 1, compounds 2 and 3 were synthesized by the general methodology of D. H. R. Barton et al., *Tetrahedron*, 43, 4297 (1987). The 2-thiono-N-hydroxypyridyl ester of Boc-Asp(OBu$^t$)-OH (7), intermediate 8, was prepared via the mixed anhydride route with isobutyl chloroformate. This ester was not isolated, but rather, was immediately irradiated in the presence of either maleimide or N-methylmaleimide (20) to give adducts 9 and 10, respectively, as diastereoisomeric mixtures. Oxidation of adduct 9 to the sulfoxide followed by pyrolysis gave the maleimido intermediate 11. A similar sequence of reactions gave the N-methylmaleimido intermediate 12 from adduct 10. Treatment of 11 and 12 with CF3CO2H, followed by cationexchange chromatography, gave the β-maleimido amino acid 2 and the β-(N-methylmaleimido) amino acid 3, respectively.

Catalytic reduction of the olefinic bond of 11 gave the reduced product as a mixture of two diasteroisomers, 13A and 13B, in a ratio of 1:1. This mixture was separated by silica gel column chromatography. No attempt was made to determine the absolute configuration of the two isomers. Deprotection of 13A and 13B with CF3CO2H followed by cation-exchange chromatography afforded the diasteroisomeric β-succinimido analogs 5A and 5B, respectively.

The synthesis of analog 4 was carried out as shown in Scheme I.

Scheme I.

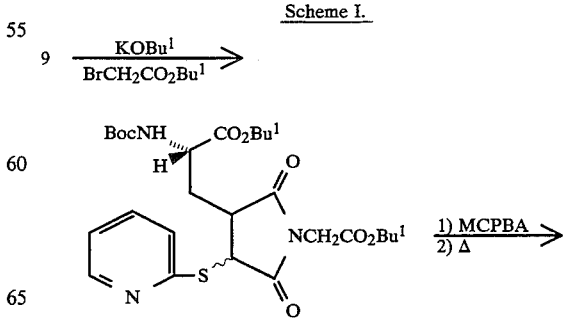

14

-continued
Scheme I.

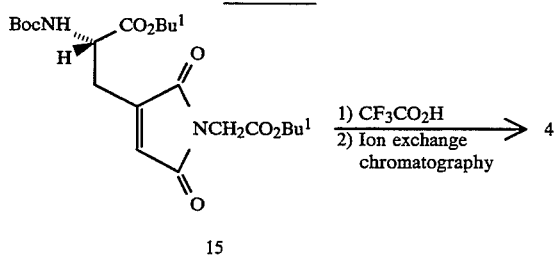

The alkylation of 9 with tert-butyl bromoacetate yielded the N-carboxymethyl adduct 14. This was confirmed by IR analysis of the N-(carboxymethyl)-maleimido intermediate 15 which was obtained from 14 by the same set of reactions used to convert 9 to 11. Structure 15 was differentiated from the possible O-alkylation product by the IR C=C stretching band. This band appeared at 1646 cm$^{-1}$ in 15. In contrast, the conjugated double bond in the O-alkylated maieimides appears at 1600cm$^{-1}$. In addition, the strong band that is observed at 1042 cm$^{-1}$ for the ether linkage in O-alkylated maleimides was not observed in 15. Two bands around 1700 and 1746 cm$^{-1}$ were observed for 15 for the imide and ester carbonyl stretching bands, respectively. Deprotection of 15 with $CF_3CO_2H$ gave the $\beta$-[N-(carboxymethyl)maleimido] amino acid 4.

A quisqualic analog (6) was also synthesized wherein the ring oxa moiety is replaced by —$CH_2$—. For preparation, see N. Subasinghe et al., *J. Med. Chem.*, 35, 4602 (1992). This analog did not exhibit the QUIS effect, but exhibited a potent stimulatory effect on CA1 region of the rat hippocampus ($IC_{50}$ ($\mu$M)=1.4±0.6).

Other compounds of formula I can be readily prepared by modifications of the present synthetic routes, as would be apparent to one of skill in the art of organic chemistry. For example, substitution of other N-alkyl or N-aryl maleimides for N-methylmaleimide will yield analogs of 3 wherein R is ($C_1$–$C_4$)alkyl, alkyl, aralkyl and the like. Likewise, substitution of bromo[($C_2$–$C_4$)alkyl]$CO_2$(t-Bu) for the $BrCH_2CO_2$(t-Bu) used in Scheme I will lead to analogs of 4 wherein R is [($C_2$–$C_4$)alkyl]-$CO_2H$. The free $\alpha$-amino group can be alkylated or arylated, and the free $CO_2H$ group or groups can be esterified as discussed above, employing suitable protecting groups for $NH_2$, NH and/or $CO_2H$, as would be apparent to those of skill in the art. For example, the Boc protecting group and the t-butyl protecting group can be employed as shown in Scheme I.

B. Bioassays

Figure 2:
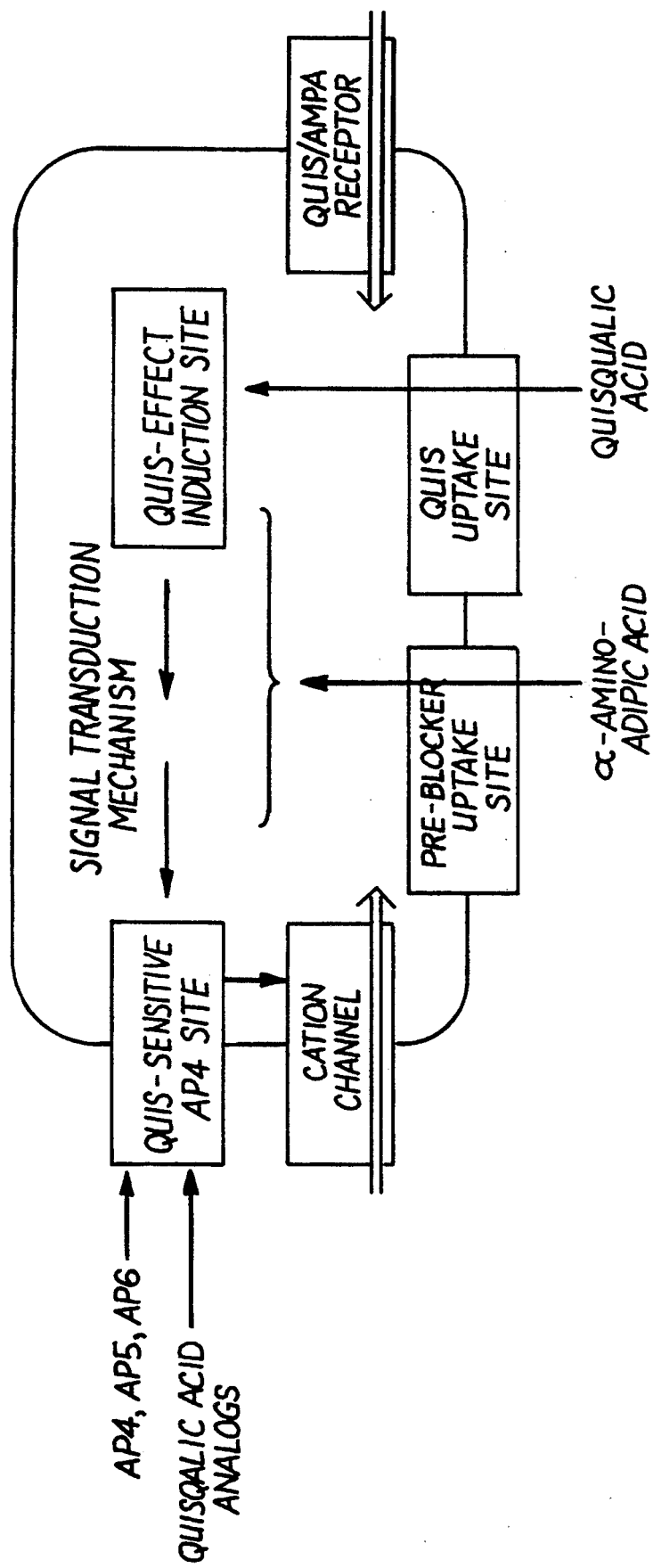
FIG. 2 is a schematic depiction of the relationship of analog uptake, quisqualic acid uptake and receptor sites in the QUIS effect.

L-Quisqualic acid analogs 2–5 were tested for their capability to induce, preblock and reverse the QUIS effect by the procedures disclosed in the examples hereinbelow. Of all of the compounds tested, only L-quisqualic acid sensitized slices to depolarization by AP4. Thus, L-quisqualic acid remains the only compound known to induce the QUIS effect. In addition, none of the analogs were capable of preblocking or reversing the sensitization induced by L-quisqualic acid. Although a thorough explanation for the unique nature of L-quisqualic acid awaits further studies, it has been suggested that induction of the QUIS effect may involve uptake of L-quisqualic acid, followed by action at an intracellular receptor. While the precise details are unknown, an induction mechanism shown in FIG. 2, involving multiple sites of interaction such as this, would explain the apparent strict structural requirements for induction, reversal and preblocking of the QUIS effect.

The $IC_{50}$ values for inhibition of the evoked synaptic field potential of CA1 neurons of analogs 2–5 were determined both before and after slices were exposed to L-quisqualic acid. Varying degrees of sensitization were observed as shown by the data on Table 2.

TABLE 2

$IC_{50}$ Values of Quisqualic Acid Analogs In the QUIS Effect[a]

| Compound | $IC_{50}$ Values ± SEM ($\mu$M) | | sensitization |
|---|---|---|---|
| | before quisqualic acid | after quisqualic acid | |
| 2 | 21 ± 4.4 | 9.5 ± 2.5 | 2.2 |
| 3 | 95 ± 19 | 6.8 ± 2.3 | 14.0 |
| 4 | 2900 ± 320 | 375 ± 75 | 7.7 |
| 5A | >10,000 | >10,000 | |
| 5B | 9200 ± 1100 | 6800 ± 930 | 1.3 |
| 6 | 1.4 ± 0.6 | 0.8 ± 0.26 | 1.7 |
| D-quisqualic acid | 78 ± 8.5 | 10 ± 1.7 | 7.5 |
| L-quisqualic acid[b] | 3.9 | 2.9 | 1.3 |
| L-AP4[b] | 1800 | 55 | 33 |
| D-AP4[b] | 2600 | 152 | 17 |

[a]Electrodes were placed in the CA1 region of the hippocampus. Potencies were determined before and after a 4-minute exposure of slices to 16 $\mu$M L-quisqualic acid. Sensitization refers to the fractional increase in potency.
[b]L-Quisqualic acid and D- and L-2-amino-4-phosphonobutanoic acid data are from Ref. 14.

The $IC_{50}$ values of analogs 3 and 4 decreased more than 7-fold after exposure of the tissue to L-quisqualic acid. Although these compounds are structurally similar to L-quisqualic acid, they do not induce the QUIS effect. Instead, they behave like L-AP4 in this system, i.e., the slices are sensitized to depolarization by these compounds following exposure to L-quisqualic acid. No significant change in $IC_{50}$ values was observed for 5A or 5B. Since compounds 2 and 6 displayed high stimulatory activity even prior to treatment of hippocampal slices with L-quisqualic acid, much of their activity may be due to action at a site which does not become sensitized by L-quisqualic acid, possibly the classical AMPA receptor.

Analogs 2–4, 5A and 5B were also found to be active at the AMPA/quisqualate receptor, one of the recognized glutamate excitatory amino acid receptors of the brain. The assay that was used was a radioligand receptor binding assay using [$^3$H]$\alpha$-amino-3-hydroxy-5-methylisoxazole-4-propionic acid ([$^3$H]AMPA) as the radioligand [Murphy et al., *Neurochemical Research*, 12, 775 (1987)]. The results are summarized on Table 3, below.

TABLE 3

Receptor Binding Activity of Quisqualic Acid Analogs at the AMPA/Quisqualate Excitatory Amino Acid Receptor

| Compound Number | % Inhibition[a] | $K_i$ |
|---|---|---|
| 2 | 93.5 | 3.7 × 10$^{-7}$ |
| 3 | 1.1 | — |
| 4 | — | — |
| 5A | 55.5 | — |
| 5B | — | — |

[a]Percent inhibition of [$^3$H]AMPA binding at a compound concentration of 10$^{-5}$ M.

The only compounds previously shown to exhibit an increase in potency following treatment of hippocampal slices with L-quisqualic acid have been certain phosphorus-containing compounds disclosed by E. R. Whittemore, *Eur. J. Pharmacol.*, 192,435 (1991) and M. K. Schulte et al., *Brain Res.*, 582,291 (1992). Thus, analogs 3 and 4 represent the first non-phosphorus compounds to which hippocampal slices are known to become sensitized. These analogs may act either at the QUIS-sensitized AP4 site described by Schulte et al., or at a different QUIS-sensitized site. The data on Table 2 also indicate that slices become sensitized to the D-isomer of quisqualic acid. This observation, in conjunction with the structural similarity of 3 and 4 to L-quisqualic acid, raises the question as to whether L-quisqualic acid itself is a ligand at a QUIS-sensitized site. The observation that compounds which preblock the QUIS effect also decrease the sensitivity of hippocampal slices for depolarization by L-quisqualic acid lends further support to the argument that quisqualic acid may be able to sensitize neurons to its own depolarization. Additionally, preblocking compounds do not block depolarization by AMPA, suggesting that depolarization of CA1 neurons by L-quisqualic acid may involve action at a QUIS-sensitized site in addition to the classical AMPA receptor.

The present analogs may be delivered directly to the CNS or PNS, i.e., by injection, or by employing nose-drops, eyedrops or ocular inserts, as well as by sublingual, buccal, transdermal or vaginal routes of administration, as are known to the art. The present compounds may also be injected or infused intravenously in combination with a pharmaceutically acceptable liquid vehicle. Effective dosages can be determined empirically by the clinician, or extrapolated from the $IC_{50}$ data derived from known neuroactive compounds used both in in vivo and in vitro animal model studies, as well as in human clinical trials.

The invention will be further described by reference to the following detailed examples, wherein melting points were determined on a Thomas-Hoover Unimelt melting point apparatus Model 6406-K and are uncorrected. Specific rotations were measured with a Rudolph Research Autopol III polarimeter at 589 nm (Na D-line) at 24° C. Elemental analyses were performed by M-H-W Laboratories, Phoenix, Ariz. Unless otherwise indicated, all analytical results were within ±0.4% of the theoretical values. $^1$H-NMR spectra were recorded on either a Varian 300-MHz, an IBM 200-MHz, an IBM 300-MHz, or a GE 300-MHz spectrometer. The chemical shifts are reported in parts per million (ppm) relative to tetramethylsilane (TMS) in $CDCl_3$ or DMSO-$d_6$ and to TSP in $D_2O$. $^{13}$C NMR was performed on either a Varian (300 MHz at 75 MHz), an IBM (200 MHz at 50 MHz or 300 MHz at 75 MHz), or a GE (300 MHz at 75 MHz) spectrometer. When DMSO-$d_6$ was used as solvent, it served as the internal standard at δ 39.5. When $D_2O$ was used, dioxane (δ 64.5) was added as the external standard. FAB mass spectra were obtained on a Kratos MS25 spectrometer. Column chromatography was performed on silica gel (Merck, grade 60, 240–400 mesh, 60 Å) from Aldrich Chemical Co. Cation-exchange chromatography was performed with AG 50W-X8 resin (100–200 mesh) obtained from Bio-Rad Laboratories. Thin-layer chromatography (TLC) was carried out on Analtech 250-μm silica gel GF Uniplates. Visualization was achieved with either UV, $I_2$, vanillin-sulfuric acid, or ninhydrin spray. D- and L-quisqualic acid were obtained from Tocris Neuramin.

EXAMPLE 1 tert-Butyl(S)-2,5-Dihydro-2,5-dioxo-α-[(tert-butoxycarbonyl) amino]-1H-pyrrole-3-propanoate (11)

Boc-Asp-OBu$^t$ (0.65 g, 2.2 mmol) was dissolved in THF (6 mL) and the solution cooled to −15° C. under an Ar atmosphere. To this solution was added N-methylmorpholine (NMM) (0.22 g, 2.2 mmol) and isobutyl chloroformate (0.30 g, 2.2 mmol). The mixture was stirred for 5 min at −15° C. To this was added a cooled (−15° C.) solution of 2-mercaptopyridine N-oxide (0.3 g, 2.6 mmol) and $NEt_3$ (0.2 g, 2.7 mmol) in THF (4 mL). The mixture was stirred for 1.5 hr at −15° C. in the dark. The solution was then rapidly filtered and the yellow filtrate was irradiated in the presence of maleimide (1.07 g, 11 mmol) with two tungsten lamps (200 W) at ambient temperature under an Ar atmosphere for 30 min. $Et_2O$ was added to the reaction mixture and the solid that precipitated was removed by filtration. The $Et_2O$ layer was washed successively with 0.1N $NaHCO_3$, $H_2O$, 0.5 N HCl, $H_2O$, and saturated NaCl. The $Et_2O$ solution was dried over anhydrous $MgSO_4$ and concentrated under reduced pressure to give a yellow oil. This was purified by silica gel column chromatography with a solvent system consisting of EtOAc and hexane (1:3) to give 0.69 g (70%) of 9 as an oil. $^1$H NMR resonances at δ 6.96–7.06, 7.12–7.24, 7.42–7.58, and 8.21–8.34 indicated that the 2-thiopyridyl moiety was presented. This mixture of diastereoisomers was used in the next reaction without further purification.

A solution of 9 (0.61 g, 1.35 mmol) in $CHCl_3$ (7 mL) was cooled to 0° C. To this solution was added a solution of m-chloroperoxybenzoic acid (MCPBA) (0.31 g, 1.42 mmol) in $CHCl_3$ (4 mL). The mixture was stirred at room temperature for 1 hr after which time $CH_2Cl_2$ was added. This solution was washed successively with 1 N $NaHCO_3$, $H_2O$, 0.5 N HCl, $H_2O$, and saturated NaCl. The solution was dried over anhydrous $MgS_4$ and stripped of solvent in vacuo and the residue dried under high vacuum for 1 hr. This material was then dissolved in anhydrous toluene and heated at reflux for 1 hr. The solvent was removed under reduced pressure and the residue was purified by silica gel column chromatography (EtOAc/hexane, 1:5) to give 0.26 g (57% from 9) of 11 as a colorless oil which solidified when cooled: mp 104°–105° C.; [α]D+9.05° (c 1.47, $CHCl_3$); Anal. ($C_{16}H_{24}N_2O_6$) C, H, N.

EXAMPLE 2

(S)-2,5-Dihydro-2,5-dioxo-α-amino-1H-pyrrole-3-propanoic Acid (2)

Compound 11 (0.4 g, 1.17 mmol) was dissolved in $CF_3CO_2H$ and the mixture was stirred at room temperature overnight. The excess $CF_3CO_2H$ was evaporated under vacuum and the resulting residue was chromatographed on a cationexchange column (AG 50W-X8) with water as the eluting solvent. The fractions containing the product were lyophilized to give 0.18 g (83%) of 2 as a white solid: mp 142° C. dec; [α]D +5° (c 0.5, $H_2O$); $^1$H NMR (300 MHz, $D_2O$) δ 3.1–3.2 (m, 2 H, $CH_2$), 4.42–4.48 (m, 1 H, α-CH), 6.76 (s, 1 H, HC=C); $^{13}$C NMR (75 MHz, $D_2O$) δ 26.02 ($CH_2$), 52.31 (α-C), 130.87 (C=CH), 144.01 (C=CH), 171.89 (C—O), 173.07 (C=O), 173.53 (C=O). Anal. ($C_7H_8N_2O_4$) C, H, N.

EXAMPLE 3 tert-Butyl (S)-2,5-Dihydro-2,5-dioxo-1-methyl-α-[(tertbutoxycarbonyl)amino]pyrrole-3-propanoate (12)

Boc-AspOBu$^t$ (5 g, 17.3 mmol) was converted to its 2-thiono-N hydroxypyridyl ester 8 in the same manner as described above in the preparation of 11. A solution of this ester was irradiated in the presence of N-methylmaleimide (9.6 g, 86.4 mmol) with two tungsten lamps (200 W) at ambient temperature under an Ar atmosphere for 1 hr. Et$_2$O was added to the reaction mixture and the solid that precipitated was removed by filtration. The Et$_2$O layer was washed successively with 0.1 N NaHCO$_3$, H$_2$O, 0.5 N HCl, H$_2$O, and saturated NaCl. The Et$_2$O solution was dried over anhydrous MgSO$_4$ and concentrated under reduced pressure to give a yellow oil. This was purified by silica gel column chromatography with a solvent system consisting of EtOAc and hexane (1:4) to give 6.47 g (80%) of 10 as an oil. This mixture of diasteroisomers was converted to 12 by the same set of reactions described above for the conversion of 9 to 11. The crude product was purified by silica gel column chromatography (EtOAc/hexane, 1:6) to give 2.5 g (50%) of 12 as a colorless oil which solidified when cooled: mp 111°–112° C.; [α]D +8.6° (c 1.22, CHCl$_3$); Anal. (C$_{17}$H$_{26}$N$_2$O$_6$) C, H, N.

EXAMPLE 4

(S)-2,5-Dihydro-2,5-dioxo-α-amino-1-methylpyrrole-3-propanoic Acid (3)

Compound 12 (1 g, 2.8 mmol) was dissolved in CF$_3$CO$_2$H (20 mL) which had been precooled in an ice bath. This mixture was stirred overnight at room temperature. The acid was removed under vacuum and the residue dried under high vacuum overnight. This residue was dissolved in water (1 mL) and subjected to cation-exchange chromatography (AG 50W-X8, column volume=3 mL). The column was eluted with water, and the fractions corresponding to product were evaporated to dryness. The residue was dissolved in a small amount of water and lyophilized to give 0.33 g (59%) of 3 as a white solid: mp 190°–194° C. dec; [α]D +2.5° (c 0.28, H$_2$O); $^1$H NMR (300 MHz, D$_2$O) δ 2.9 (s, 3 H, CH$_3$), 2.96–3.0 (m, 2 H, CH$_2$), 3.97 (dd, J=6.41 and 7.02 Hz 1 H α-CH ) 6.6 (m, 1 H, C═CH ); $^{13}$C NMR ( 75 MHz, D$_2$O) δ 23.53 (CH$_3$), 26.57 (CH$_2$), 52.96 (α-C), 130.07 (C═C), 143.79 (C═C), 172.59 (C═O), 172.72 (C═O), 173.01 (C═O). FAB-MS m/z 199 (MH)+. Anal. (C$_8$H$_{10}$N$_2$O$_4$.1/3H$_2$O) C, H, N.

EXAMPLE 5 tert-Butyl 2,5-Dioxo-α(S)-[(tert-butoxycarbonyl)amino]3(RS)-pyrrolidinepropanoate (13A and 13B).

A solution of 11 (0.3 g, 0.88 mmol) dissolved in methanol (2 mL) was placed in a Parr bottle along with 10% Pd/C (30 mg). The contents were subjected to a hydrogen pressure of 46 psi and shaken on a Parr apparatus for 5.5 hr. The resulting solution was filtered and the MeOH evaporated under vacuum to give a colorless oil, which yielded a gelatinous solid upon trituration with EtOAc and hexane. The diasteroisomers were separated by silica gel column chromatography (ratio of compound to silica gel was 1:200) with EtOAc/hexane (1:3) as the eluting solvent. The elution was carried out over a period of two days and yielded 92 mg (30.5%) of 13A and 115.5 mg (38.3%) of 13B as gelatinous solids.

EXAMPLE 6

2,5-Dioxo-α(S)-amino-3(RS)-pyrrolidinepropanoic Acid (5A and 5B)

Diasteroisomers 13A (0.07 g, 0.2 mmol) and 13B (0.1 g, 0.29 mmol) were each deprotected by the same procedure as that described above for the synthesis of 3 to give 5A and 5B, respectively. Both were isolated as white solids after lyophilization.

5A: Yield=25 mg (65%); mp 216°–219° C. dec; [α]D −3.04° (c 0.69, H$_2$O); $^1$H NMR (300 MHz D$_2$O) δ 2.0–2.24 (m, 2 , H, β—CH$_2$), 2.44 (dd, J=5.4 and 18.1 Hz, 1 H, CH$_2$), 2.88 (dd, J=8.79 and 18.1 Hz, 1 H, CH$_2$), 2.96–3.01 (m, 1 H, CH), 3.77 (t, J=6.0 Hz, 1 H, α-CH); $^{13}$C NMR (75 MHz, D$_2$O) δ 31.07 (CH$_2$), 35.55 (CH$_2$), 37.87 (CH), 52.80 (α-C), 173.35 (C═O), 180.91 (C═O), 183.33 (C═O); FAB-MS m/z 187 (MH)+. Anal. (C$_7$H$_{10}$N$_2$O$_4$.2/3H$_2$O) C, H, N.

5B: Yield=36.7 mg (68%); mp 228°–230° C. dec; [α]D +27.9° (c 0.62, H$_2$O); $^1$H NMR (300 MHz, D$_2$O) δ 2.04–2.15 (m, 2 H, β—CH$_2$), 2.47 (dd, J=5.4 and 18 Hz, 1 H CH$_2$), 2.89, (dd, J=9.3 and 18 Hz, 1 H, CH$_2$), 3.0–3.1 (m, 1 H, CH), 3.68 ( t, J=5.7 Hz, 1 H, α-CH ); $^{13}$C NMR ( 75 MHz, D$_2$O ) δ 31.72 (CH$_2$), 35.39 (CH$_2$), 38.87 (CH), 53.44 (α-C), 173.72 (C═O), 180.86 (C═O), 183.24 (C═O); FAB-MS m/z 187 (MH)+.

EXAMPLE 7 tert-Butyl(S)-2,5-Dihydro-2,5-dioxo-1-[(tert-butoxycarbonyl)methyl]-α-[(tert-butoxycarbonyl)amino]pyrrole-3-propanoate (15)

Compound 9 (0.95 g, 2.1 mmol) was dissolved in dry DMF (50 mL). To this solution was added potassium tert-butoxide (0.26 g, 2.3 mmol) and the mixture stirred for 45 min at room temperature. tert-Butylbromoacetate (1.9 g, 9.7 mmol) was added and the mixture stirred for a further 3.5 hr at room temperature. DMF was removed by rotoevaporation under high vacuum at 40° C. The resulting crude mixture was purified by column chromatography with EtOAc/hexane (1:2) as the eluting solvent to give 0.8 g (67%) of 14 as an oil. The presence of the 2-thiopyridyl moiety was shown by the $^1$H NMR resonances at δ 6.93–7.04, 7.15–7.24, 7.44–7.6, and 8.29–8.39. This material was directly converted to 15 by the same set of reaction conditions used above in the conversion of 9 to 11. The crude product was purified by silica gel column chromatography (EtOAc/hexane, 1:7). The oil which was obtained gave a white solid upon trituration with cold hexane. Recrystallization of this solid from hexane gave 0.38 g (59%) of 15: mp 88.5°–89.5° C.; [α]D +11.4° (c 0.51, CHCl$_3$); FAB-MS m/z 455 (MH)+. Anal. (C$_{22}$H$_{34}$N$_2$O$_8$) C, H, N.

EXAMPLE 8

(S)-2,5-Dihydro-2,5-dioxo-α-amino-1-(carboxymethyl)-pyrrole-3-propanoic Acid (4)

Compound 15 (0.3 g, 0.66 mmol) was deprotected using the same method as that used to make 3 to yield 0.11 g (68.8%) of 4 as white solid: mp 125° C. dec; [α]D −3.0° (c 0.61, H$_2$O); $^1$H NMR (300 MHz, D$_2$O) δ 2.9–3.1 (m, 2 H, CH$_2$), 4.07 (dd, J=6.1 and 7.32 Hz, 1 H, α-CH), 4.18 (s, 2 H, NCH$_2$), 6.69 (s, 1H, C═CH); $^{13}$C NMR (75 MHz, D$_2$O) δ 26.29 (CH$_2$), 39.38 (α-C), 52.33 (NCH$_2$), 130.51 (C═C), 143.72 (C═C), 171.14 (C═O), 171.72 (C=O), 171.96 (C=O), 172.52 (C=O); FAB-MS m/z 243 (MH)+. Anal. ($C_9H_{10}N_2O_6 \cdot 1/3H_2O$) C, H, N.

EXAMPLE 9

Bioassays

A. Tissue Preparation

Transverse hippocampal slices were obtained from 30–100 day-old male Sprague-Dawley rats. Rats were anesthetized with urethane (1.5 g/kg ip) and then decapitated. The brain was removed and placed in ice-cold preparatory medium comprised of 124 mM NaCl, 3.3 mM KCl, 10 mM $MgSO_4$, 0.5 mM $CaCl_2$, 1.2 mM $KH_2PO_4$, 10 mM glucose, and 26 mM $NaHCO_3$ equilibrated with 95% $O_2$/5% $CO_2$ (pH 7.4). The hippocampus was then isolated and sliced into 500-μm slices using a Campden Instruments VibroSlice microtome. Slices were submerged in preparatory medium at 28° C. which was aerated with 95% $O_2$/5% $CO_2$ and incubated for 45 min. Slices were then transferred to recording medium comprised of 124 mM NaCl, 3.3 mM KCl, 2.4 mM $MgSO_4$, 2.5 mM $CaCl_2$, 1.2 mM $KH_2PO_4$, 10 mM glucose, and 26 mM $NaHCO_3$ aerated with 95% $O_2$/5% $CO_2$ (pH 7.4) and incubated at 28° C. for at least 30 min. prior to use.

B. Electrophysiology

Slices were transferred to a small recording chamber containing the recording medium at 34° C. Initially, the upper surface of the slice was exposed to a humid atmosphere containing 95% $O_2$/5% $CO_2$. Bipolar stimulation (0.1 ms, 10–40 V, 0.1 Hz) was delivered to the Schaffer collateral axons via a pair of Teflon-coated stainless steel wires (0.003 in.). Glass microelectrodes (2–14 MΩ impedance filled with 2 M NaCl) were placed in the stratum radiatum of region superior to serve as recording electrodes. The evoked extracellular synaptic field potentials were observed using a storage oscilloscope, and the peak amplitudes were sampled and recorded with a chart recorder. When a suitable field potential was obtained, the slice was submerged in oxygenated medium (34° C.) and the response allowed to stabilize. Test compounds were dissolved in oxygenated medium and were added and removed using a push/pull device allowing a complete change of medium within 30 sec.

Slices were exposed to L-AP4, L-quisqualic acid and the test compound in the following sequence, which is a modification of the previous method: (1) 200 μM L-AP4, (2) test compound, (3) 200 μM L-AP4, (4) 16 μM L-quisqualic acid, (5) 200 μM L-AP4, (6) test compound, (7) 200 μM L-AP4. Slices were washed between each addition of new drug until the peak amplitude of the field potential returned to its pretest level. Full concentration-response curves were determined for the test compound both before and after treatment of slices with L-quisqualic acid. In addition to determining the potency of compounds before and after addition of L-quisqualic acid, this protocol was designed to test for the ability of test compounds to induce the QUIS effect (and thus mimic the effects of L-quisqualic acid) and to test for the "preblocking" and "reversal" effects which have been previously observed only for L-homocysteine sulfinic acid, L-serine O-sulfate, and L-α-aminoadipic acid.

C. Concentration-Response Data

Concentration-response data were obtained by exposing the slice to a concentration of drug which was subthreshold for inhibition of the field potential. Drug concentration was doubled every 4 min until the response had either declined more than 70% or the bath concentration of the drug exceeded 10 mM. A 4-min exposure has been shown to allow sufficient time to equilibrate the slice with the drug. $IC_{50}$ values were obtained by plotting the fractional response remaining at the end of 4 min versus the log of the bath concentration of the drug. The concentration which produced a 50% inhibition of the peak amplitude ($IC_{50}$) was interpolated from the graph. All reported $IC_{50}$ values are the mean values for four or more experiments. The results are summarized on Table 2, above.

All publications, patents and patent documents are incorporated by reference herein, as though individually incorporated by reference. The invention has been described with reference to various specific and preferred embodiments and techniques. However, it should be understood that many various and modifications may be made while remaining with the spirit and scope of the invention.

WHAT IS CLAIMED IS:

1. A compound of the formula:

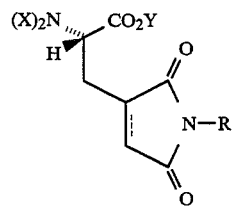

wherein R is H, ($C_1$-$C_4$)alkyl, ($C_3$-$C_6$)cycloalkyl, ($C_3$-$C_6$)cycloalkyl($C_1$-$C_4$)alkyl, allyl, ($C_6$-$C_{10}$)aryl or ($C_1$-$C_4$)alkyl$CO_2Y$; Y is H, ($C_1$-$C_4$)alkyl or ($C_6$-$C_{10}$)aryl; each X is individually H, ($C_1$-$C_4$)alkyl, ($C_6$-$C_{10}$)aryl, ($C_3$-$C_6$)cycloalkyl($C_1$-$C_4$)alkyl or ($C_3$-$C_6$)cycloalkyl; the bond represented by —is present or is absent; and the pharmaceutically acceptable salts thereof.

2. The compound of claim 1 wherein R is H or ($C_1$-$C_4$)alkyl.

3. The compound of claim 1 wherein Y is H or ($C_1$-$C_4$)alkyl.

4. The compound of claim 1 wherein X is H or ($C_1$-$C_4$)alkyl.

5. The compound of claim 1 wherein the bond represented by —is present.

6. The compound of claim 5 wherein R is H, $CH_3$ or $CH_2CO_2H$.

7. The compound of claim 1 wherein Y is H.

8. The compound of claim 7 wherein each X is H.

9. The compound of claim 1 wherein the bond represented by —is absent.

10. The compound of claim 9 wherein R is H.

11. The compound of claim 10 wherein Y is H.

12. The compound of claim 11 wherein each X is H.

13. (S)-2,5-Dihydro-2,5-dioxo-α-amino-1H-pyrrole-3-propanoic acid.

14. (S)-2,5-Dihydro-2,5-dioxo-α-amino-1-methylpyrrole-3-propanoic acid.

15. 2,5-Dioxo-α(S)-amino-3(RS)-pyrrolidinepropanoic acid.

* * * * *